United States Patent [19]

Modell

[11] Patent Number: 5,022,757
[45] Date of Patent: Jun. 11, 1991

[54] HETERODYNE SYSTEM AND METHOD FOR SENSING A TARGET SUBSTANCE

[76] Inventor: Mark D. Modell, 321 Tappan St., Brookline, Mass. 02164

[21] Appl. No.: 299,315

[22] Filed: Jan. 23, 1989

[51] Int. Cl.$^5$ .................... G01N 21/64; G01N 21/49
[52] U.S. Cl. .................................. 356/318; 128/633; 250/458.1; 250/459.1; 356/342; 356/349
[58] Field of Search ............... 356/317, 318, 336, 338, 356/343, 349; 250/458.1, 459.1, 461.1, 461.2; 128/633

[56] References Cited

U.S. PATENT DOCUMENTS

| | | | |
|---|---|---|---|
| 4,109,647 | 8/1978 | Stern et al. | 356/28 |
| 4,249,540 | 2/1981 | Koyama et al. | 128/666 |
| 4,259,009 | 3/1981 | Jernigan | 356/1 |
| 4,346,991 | 8/1982 | Gardner et al. | 356/28.5 |
| 4,483,614 | 11/1984 | Rogers | 356/318 |
| 4,577,963 | 3/1986 | Traina | 356/88.5 |
| 4,590,948 | 5/1986 | Nilsson | 128/666 |
| 4,594,510 | 6/1986 | Brown et al. | 250/341 |
| 4,627,730 | 12/1986 | Jungerman et al. | 356/349 |
| 4,631,581 | 12/1986 | Carlsson | 356/318 |

OTHER PUBLICATIONS

Stevenson et al., "Applications of Non-Intrusive Instrumentation in Fluid Flow Research" papers and discussion of the Fluid Dynamics Panel Symposium held at the French-German Research Institute (ISL), Saint-Louis, France May 3-5, 1976.

Andersson et al., "Fluorescence Endoscope Instrumentation for Improved Tissue Characterization" Medial Physics, vol. 14, #4, Jul./Aug. 1987, pp. 633-636.

Baumgartner et al., "A Fluorescence Imaging Device for Endoscopic Detection of Early Stage Cancer Instrumental & Experimental Studies" Photochemistry & Photobiology, vol. 46, #5, pp. 759-763, 1987.

Kaufman, "Fiberoptics in Laser Doppler Velocimetry, Lasers & Applications" Jul. 1986, pp. 71-73.

Primary Examiner—Vincent P. McGraw
Attorney, Agent, or Firm—Robert M. Asher

[57] ABSTRACT

A system and method for sensing a target substance in a medium by directing at least first and second beams of radiation to intersect within the medium and establish one or more sensing volumes. The beams have different frequencies to generate a beat frequency at the sensing volume. A selected optical effect, based on an optical property of the target substance within the sensing volume, on the first and second beams is detected at at least one selected spectral line. A signal is generated representative of the selected optical effect, such as absorbance or fluorescence, and the portion of the signal which is substantially at the beat frequency is combined with at least one selected value to determine the amount of the target substance.

27 Claims, 4 Drawing Sheets

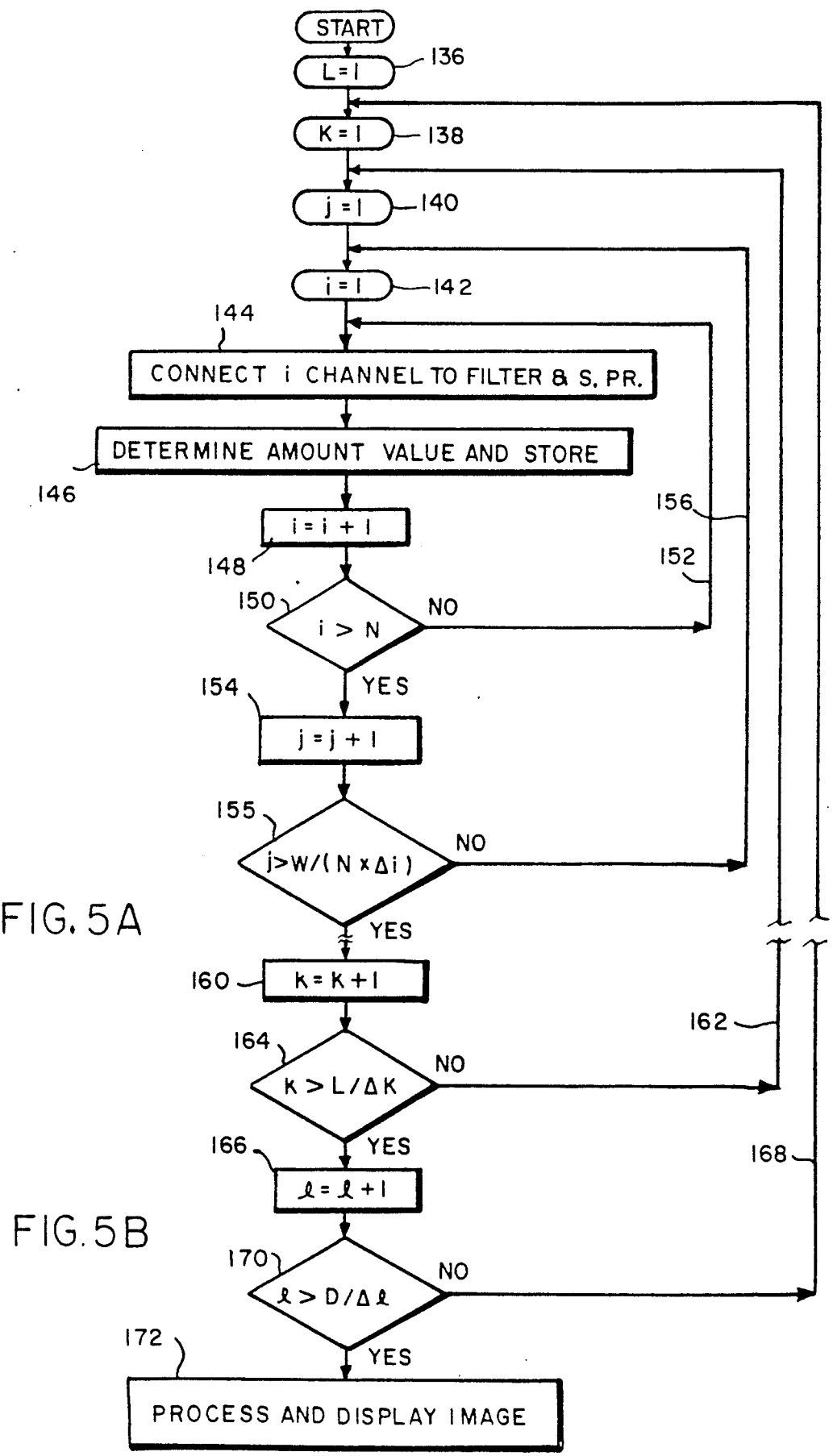

HETERODYNE SYSTEM AND METHOD FOR SENSING A TARGET SUBSTANCE

FIELD OF INVENTION

This invention relates to a system and method for sensing a target substance such as a tumor or a dye within the tumor, and more particularly to such a system and method which sense the target substance based on an optical effect on two or more beams of radiation, the beams generating one or more beat frequencies which are selectively observed to determine the amount of the target substance.

BACKGROUND OF INVENTION

There are a number of fields in which it is desirable to locate and identify a target substance within a medium. In the medical field, it is desirable to optically detect cancerous tissue, plaque on arterial walls, and other selected substances.

One technique for diagnosing the presence of a tumor uses photodynamic sensitizers, for example dyes such as hematoporphyrin derivative (HPD), Rhodamine 123, and merocyanine, which are injected into the human or animal body, where they are selectively retained by cancerous tissue. After a predetermined period of time, typically two or three days after injection, significantly high levels of photodynamic sensitizer are retained in malignant tissue relative to levels in normal tissue. When irradiated with ultraviolet or short wavelength visible light, the higher concentrations of photodynamic sensitizer within the malignant tissue exhibit a fluorescence at a color substantially different from the light pink appearance of normal tissue. For example, HPD exhibits a bright red fluorescence. See Baumgarthner et al., Photochem and Photobiol., Vol. 46, pp. 1–11 (1987); and Anderson et al., Med. Phys. Vol. 14, pp. 623–636 (1987).

Presently, however, it is difficult to optically detect malignant tissue that does not lie on the surface of the tissue being examined. The deeper the target lies within the tissue, the greater the amount of dye which is activated by the radiating beam of light. In other words, a deeply penetrating beam induces fluorescence along its entire path. Such devices therefore suffer from a low signal-to-noise ratio.

In an entirely different application, there are a number of systems which measure the velocity of moving particles using two beams which are at slightly different frequencies from each other. The intersection of the beams produces a beat frequency, also known as a heterodyne effect. The velocity of moving particles is determined by measuring the Doppler shift induced in the beat frequency; in other words, the greater the particle velocity, the greater the observed frequency is shifted from the original beat frequency. Several systems then use the Doppler shift information to determine particle concentration. Such systems, however, are designed to observe particles moving through a fluid.

SUMMARY OF INVENTION

It is therefore an object of this invention to provide an improved optical detection system which generates a readily detectable optical signal within a selected sensing volume of a medium.

It is a further object of this invention to provide such a system and method which can control the depth of the selected sensing volume.

A still further object of this invention is to provide an improved system and method for detecting tumors and other target tissue within a patient.

Yet another object of this invention is to provide such a system and method which is harmless, non-invasive, and inexpensive.

It is a further object of this invention to improve signal-to-noise ratio and therefore improve depth of sensing.

This invention results from the realization that truly effective sensing of a target substance, such as a photodynamic sensitizer selectively retained within a tumor, can be achieved by directing first and second beams of radiation to intersect within a medium and establish a sensing volume, the beams being at different frequencies to generate a beat frequency at the sensing volume, detecting a selected optical effect such as absorbance or fluorescence which is based on an optical property of the target substance, and combining one or more selected values with only the portion of the detected optical effect which is at the beat frequency, to determine the amount of the target substance.

This invention features a system for sensing a target substance in a medium. The system includes transmission means for directing first and second beams of radiation to intersect within the medium and establish a sensing volume, the beams having different frequencies to generate a beat frequency at the sensing volume. The system further includes means for detecting a selected optical effect, based on an optical property of the target substance within the sensing volume, on the first and second beams at at least one selected spectral line and for generating a signal representative of the selected optical effect. Signal filter means passes only the portion of the signal which is substantially at the beat frequency to produce a beat portion signal, and the system further includes means for combining the beat portion signal with a selected value to determine the amount of the target substance.

In one embodiment, the means for combining includes means for matching the beat portion signal with a threshold value as the selected value and for indicating when the threshold value is exceeded. Alternatively, the means for combining combines the beat portion signal with at least one substance proportionality factor as the selected value. The means for combining includes means for multiplying each of a plurality of substance proportionality factors with corresponding portions of the beat portion signal representing the selected optical effect at successive selected spectral lines. Alternatively, the means for combining includes means for multiplying a single substance proportionality factor with a portion of the beat portion signal representing the selected optical effect at a plurality of selected spectral lines. The substance proportionality factor may represent a predetermined relationship between the amount of the target substance and the magnitude of the beat portion signal, and the means for combining includes means for storing the substance proportionality factor or means for calculating the substance proportionality factor according to the recited relationship. The means for detecting includes means for measuring absorbance, fluorescence, scattering, or other phenomena as the selected optical effect at the selected spectral line.

The transmitter means may include means for producing the first and second beams of radiation, such as first laser means for producing an initial beam, and beam splitter means for separating the initial beam into the first and second beams. The transmitter means may further include means for shifting the frequencies of the first and second beams relative to each other. Additionally, the transmitter means may further include means for modulating the initial beam or the first and second beams at a predetermined frequency, and means for synchronizing the detection of the optical effect at the frequency. The transmitter means may also include scanner means for redirecting the first and second beams to alter the location of the sensing volume within the medium. The scanning means may produce a depth signal indicative of the depth of the sensing volume within the medium, and the means for combining includes means, responsive to the depth signal, for supplying a different selected value as the depth changes.

This invention also features a system for sensing a target substance in a medium, including first transmitter means for directing first and second beams of radiation to establish a first sensing volume and generate a first beat frequency, and second transmitter means for directing third and fourth beams of radiation to intersect and establish a second sensing volume and establish a second beat frequency. Detector means detects a first selected optical effect on the first and second beams and detects a second selected optical effect, which may be the same or different from the first selected optical effect, on the third and fourth beams at at least one selected spectral line, and generates a signal representative of the first and second selected optical effects. The first and second beat frequencies may be the same or different from each other, and the first and second optical effects may be the same or different, and may be based on the same or different optical properties. The system further includes signal filter means for passing only the portions of the signal which are substantially at the first and second beat frequencies to produce a beat portion signal, and means for combining the beat portion signal with one or more selected values to determine the amount of the target substance. The portion of the beat portion signal representing the first and second beat frequencies may be combined with the same or different selected values, respectively.

This invention further features a method of sensing a stationary target substance in a medium such as a patient, comprising directing first and second beams of radiation to intersect within a medium and establish a sensing volume, detecting a selected optical effect on the first and second beams and for generating a signal representative of the selected optical effect. The portion of the signal which is substantially at the beat frequency is combined with at least one selected value to determine the amount of the target substance.

In one embodiment, two or more additional sensing volumes are established, the sensing volumes are successively shifted through the medium to successive positions, and an image of the target substance is produced based on successive determinations of the amount of the target substance at the successive positions.

DISCLOSURE OF PREFERRED EMBODIMENT

Other objects, features and advantages will occur to those skilled in the art from the following description of a preferred embodiment and the accompanying drawings, in which:

FIGS. 5A and 5B are flow charts illustrating the operation of the beat portion combining circuit shown in FIG. 2;

This invention may be accomplished by a system which senses a target substance in a medium by directing first and second beams of radiation to intersect within the medium and establish a sensing volume. The first beam has a different frequency from the second beam to generate a beat frequency at the sensing volume. The system detects a selected optical effect on the first and second beams at at least one selected spectral line and generates a signal representative of the selected optical effect. The optical effect, such as absorbance, fluorescence, elastic scattering or Raman scattering, is based on an optical property of the target substance within the sensing volume. The system further filters the signal to pass only the portion of the signal which is substantially at the beat frequency to produce a beat portion signal. The beat portion signal is combined with a selected value such as a threshold value or a substance proportionality factor to determine the amount of the target substance.

Figure 1:
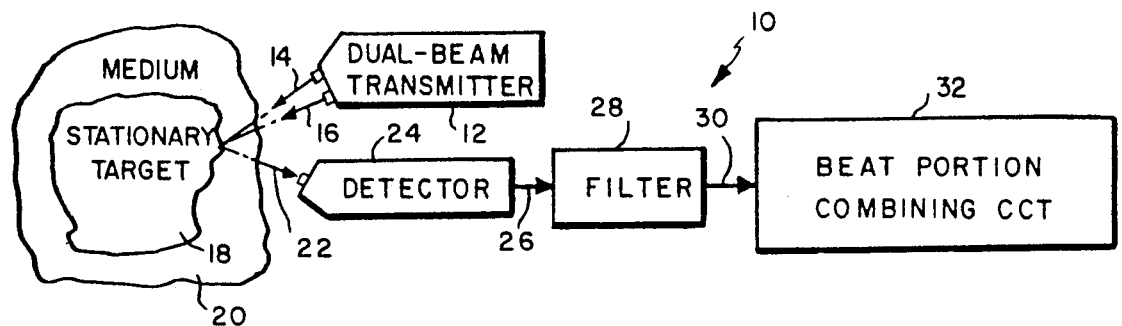
FIG. 1 is a schematic block diagram of a heterodyne system according to the present invention.

Heterodyne system 10 according to this invention, FIG. 1, includes dual beam transmitter 12 which directs beams 14, 16 to intersect at stationary target 18 within medium 20. Beams 14 and 16 have frequencies which differ sufficiently from each other to generate a beat frequency. Beating, also referred to as heterodyning, is generated at the intersection of the beams to establish a sensing volume. Returned radiation 22 is received by detector 24. As is described in more detail below, detector 24 detects a selected optical effect on beams 14 and 16. The optical effect, such as absorption, is based on an optical property, such as absorptivity, of the portion of target 18 within the sensing volume. An electrical signal is generated and supplied through line 26 to filter 28 to represent the selected optical effect on the first and second beams. Filter 28 is an electrical narrow band pass filter which passes only the portion of the signal which is substantially at the beat frequency generated by beams 14 and 16. The passed portion of the signal, referred to as the beat portion signal, is provided through line 30 to beat portion combining circuit 32 which combines the beat portion signal with one or more selected values to determine the amount of the target substance.

Figure 3:
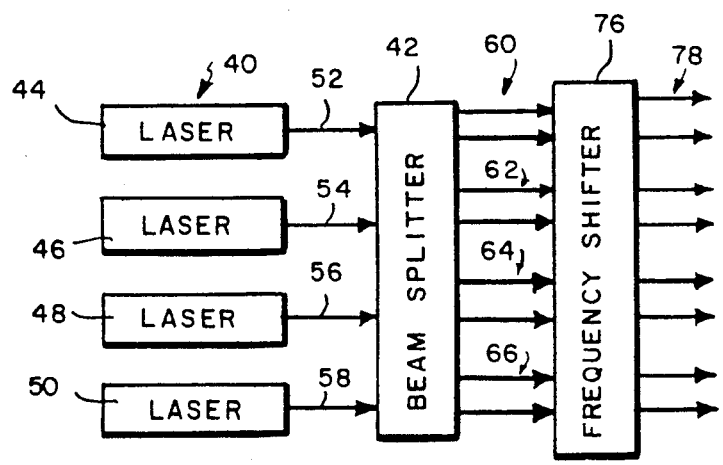
FIG. 3 is a view along lines 3—3 of FIG. 2 of the laser array, beam splitter and frequency shifter of the system of FIG. 2.
Figure 2:
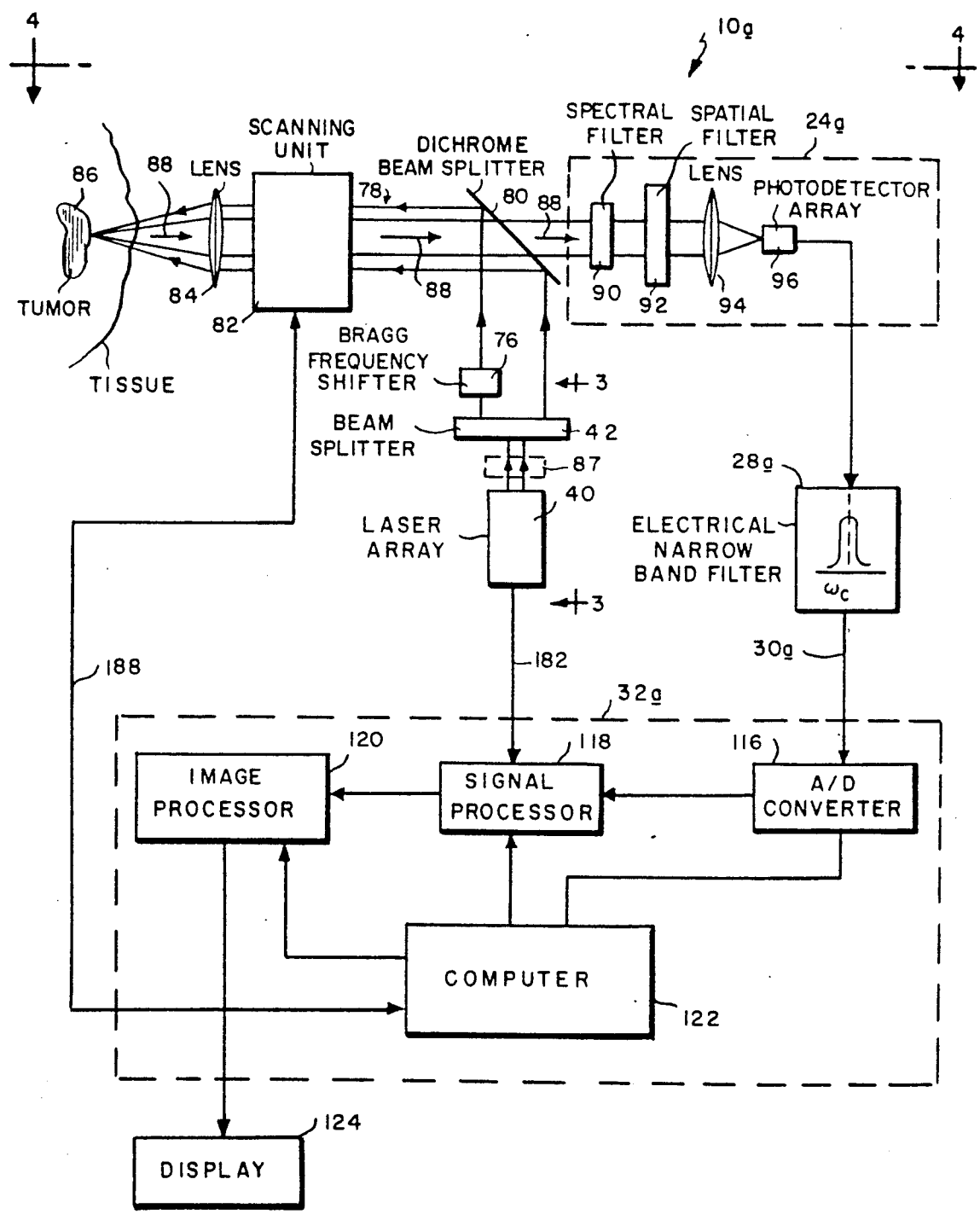
FIG. 2 is a more detailed diagram of a heterodyne system according to this invention having an array of lasers.

Heterodyne system 10a, FIG. 2, represents a preferred application of a system according to this invention, which produces an image of a selected tissue within a patient. Laser array 40 directs single beams of individual lasers through beam splitter 42 to produce a pair of beams for each laser 44, 46, 48, 50 as shown in FIG. 3. For sensing the presence of a substance such as hematoporphyrin derivative (HpD), laser model no. 164-16 (krypton ion laser) available from Spectra-Physics, Mountain View, Calif. which generates a beam having a wavelength of 405 nm is acceptable. After beams 52, 54, 56, 58 are divided into beam pairs 60, 62, 64, and 66 respectively, collectively referred to hereinafter as beam pairs 78, one of each beam pair is shifted in frequency by frequency shifter 76, such as a Bragg cell. In an alternative construction, the splitting of the beam and the shifting of the frequency are accomplished by a single element. Beam pairs 78 are then directed to dichroic beam splitter 80, FIG. 2, which directs beam pairs 78 through scanning unit 82 and lens 84 to intersect and establish successive sensing volumes at tumor 86. The nature of the sensing volumes and their movement by scanning unit 82 is described in relation to FIG. 6 below.

Figure 4:
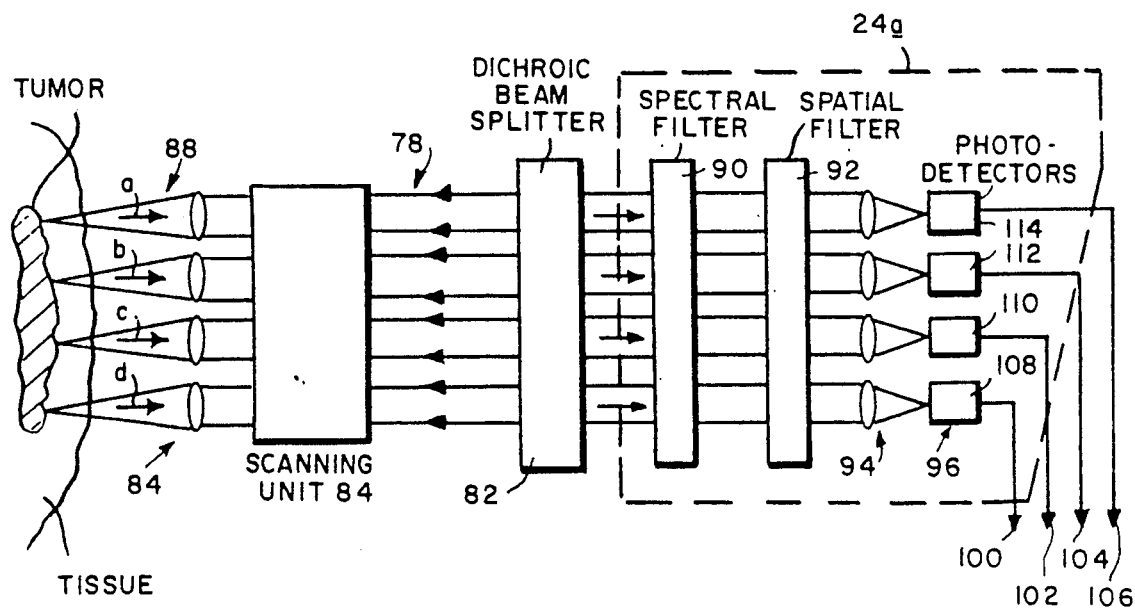
FIG. 4 is a view along lines 4—4 of FIG. 2 of the transmitting and receiving portions of the system of FIG. 2.

Returned radiation 88 passes through lens 84, scanning unit 82, and beam splitter 80 where it is received by detector 24a. Detector 24a includes spectral filter 90, spatial filter 92, lens 94 and photodetector array 96. As shown in more detail in FIG. 4, returned radiation 88 is comprised of four beams a, b, c, and d. In this construction, the returned radiation from each of the four sensing volumes is focused separately by lens arrays 84, 94 and separately detected by individual photodetectors within photodetector array 96. Alternatively, a single detector is used and the returned radiation is distinguished on different beat frequencies which are generated by the different beam pairs within beam pairs 78.

Further enhancement of optical reception is accomplished by spatial filter 92 which is positioned to block radiation emanating from another focal distance. In this construction, spatial filter 92 includes a separate aperture for each beam a, b, c, and d. Further, spectral filter 90 selectively passes predetermined wavelengths. Examples of spectral and spatial filters are described for example in Brown et al., U.S. Pat. No. 4,594,510, incorporated herein by reference.

Signals 100, 102, 104 and 106 from photodetectors 108, 110, 112 and 114, respectively, are provided to electrical narrow band filter 28a which passes only the portion of each signal which is at the beat frequency. Preferably, each of beam pairs 78 generates a different beat frequency to augment separate processing of returned radiation a, b, c, and d. A beat portion signal is generated which can be multiplexed along a single line 30a, or provided along four separate lines to beat portion combined circuit 32a. The signal is digitized by analog-to-digital converter 116 and the digitized signal is provided to signal processor 118. After an amount value is determined for the target substance for a particular coordinate, the amount values with their corresponding coordinates are provided to image processor 120 which assembles an image of tumor 86 that is provided to display 124. The operation of system 10a is coordinated by computer 122.

Modulator 87, shown in phantom, is provided in one construction between laser array 40 and beam splitter 42, or between beam splitter 42 and beam splitter 80, to modulate initial beams 52, 54, 56, 58 or beam pairs 78, respectively. Modulator 87 supplies modulation signals to signal processor 118 or computer 122 to enable synchronizing of detection of the optical effect at each sensing volume with the modulation frequency.

Figure 6:
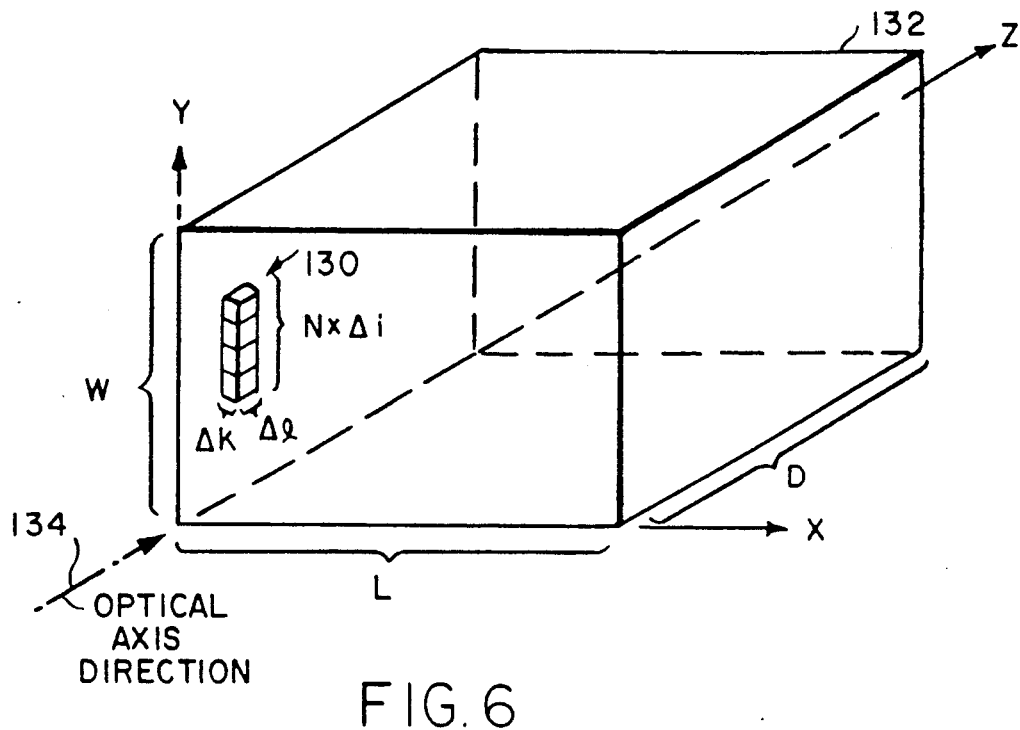
FIG. 6 is a schematic diagram representing the sensing volumes established by the system of FIG. 2 in a medium.

The operation of heterodyne system 10a is illustrated in FIGS. 5A and 5B. The system is initialized by setting the position of the four sensing volumes, referred to as a sensing volume array, relative to X, Y, and Z coordinates. These coordinates are illustrated in FIG. 6 for sensing volume array 130 within medium 132. Dashed arrow 134 represents the optical axis direction of heterodyne system 10a. Depth position l, length position k, and width position j are each set to "one" in steps 136, 138, and 140, FIG. 5A. Position l is measured along the Z axis, position k is measured along the X axis, and the position j is measured along the Y axis. Further, the channel number i is set to "one", step 142. In this construction, each beam pair from one of lasers 44, 46, 48 and 50 is designated as a separate channel. Alternatively, a number of different channels can be established for each laser by successively optically H shifting the beams. The $i^{th}$ channel is connected to filter 28a and signal processor 118, step 144 and the amount value is determined and stored, step 146. This step is shown in more detail in FIG. 7 below. The $i^{th}$ channel is incremented, step 150, and if i is less than or equal to number N, representing the total number of channels, operation returns to step 144 through loop 152. If channel i is greater than the total number of channels, width position j is incremented, step 154 and loop 156 is executed until sensing volume array 130 has been moved through the entire width dimension W, step 155.

The number of passes through loop 156 depends on the dimension of sensing volume array 130 along the Y axis; the array dimension is represented by the product of dimension delta i for each sensing volume and the total number N of sensing volumes. In this example, N is equal to 4. In one example, delta i, delta k and delta l are each one millimeter.

After sensing is accomplished along the entire width W, scanning unit 82 is commanded by computer 122 to redirect sensing volumes along the X axis for length L. This is accomplished by implementing length position k, step 160, FIG. 5B, and executing loop 162 until k is determined to be greater than length L divided by dimension delta k of the sensing volumes along the X axis, as determined in step 164. Depth position l is then incremented, step 166 and loop 168 is executed until length position k is greater than depth D divided by dimension delta l of the sensing volume along the Z axis, step 170. The image is then conventionally processed and displayed, step 172.

Figure 7:
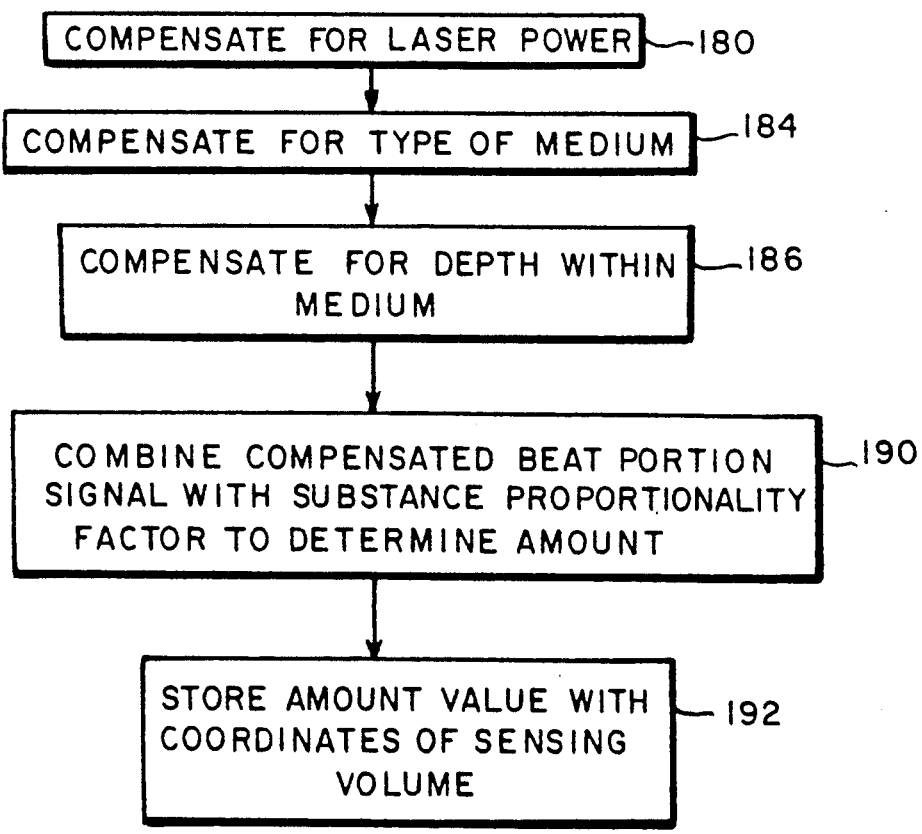
FIG. 7 is a flow chart illustrating in more detail the operation of the signal processor shown in FIG. 2.

The operation of signal processor 118 is shown in more detail in FIG. 7. After a particular channel is connected to the signal processor, the beat portion signal for that channel is compensated for laser power, step 180. The magnitude of the power is determined by a sensor within laser array 40, FIG. 2, and provided along line 182 to signal processor 118. The signal is then compensated for the type of medium, step 184, FIG. 7. In this example, the characteristic for the tissue in which tumor 86 lies is stored in computer 122 and provided to signal processor 118. The signal is then compensated for the depth of the sensing volume within the medium, step 186, as determined by a depth signal provided by scanning unit 82, FIG. 2, through line 188, FIG. 7. Each medium has different transmissivity characteristics, and the depth within that medium determines the effect of the medium on the optical signal.

The compensated beat portion signal is then combined with a substance proportionality factor to determine the amount of the target substance. step 190. This example assumes that the F number of the system remains constant. Further, conventional signal processing, including signal averaging, can be performed on the signal before or after compensation. Once the amount has been determined, the amount value is stored with the coordinates of the sensing volume for that reading, step 192.

Image processor 120 can record and display each and every coordinate point and its accompanying amount value, or can provide an outline of a target using boundary coordinates to compress the image within memory. Alternatively, the image processor can simply record changes in amplitude of the amount value.

Scanning unit 82 can operate by "start/stop" sensing as described or by continuous, "on-the-fly" sensing in which the sensing volume is continuously moved through the medium. Moreover, scanning unit 82 and image processor 120 can operate to track the border of a target such as tumor 86.

To obtain more accurate sensing of the target substance, it is desirable to utilize at least two channels for the same sensing volume. For differential absorption, beams from two or more lasers can be successively directed to the same sensing volume, each laser providing beams with different optical frequencies. Alternatively, a single laser can be used with an optical shifter that sequentially changes the optical frequency of the beam pair. For fluorescence, for example, dual readings can be obtained by first detecting radiation at the excitation frequency of the beams, and then detecting radiation at the fluorescence frequency. Spectral filter 90, FIG. 2 can be altered accordingly to accommodate the two different optical frequencies. Alternatively, two readings can be obtained by first sensing normal tissue and then sensing tissue with the target substance such as a tumor or a dye within the tumor.

As indicated above, the selected value with which the beat portion signal is combined can be a threshold value or a substance proportionality factor. For a system which does not require calibration, the operation shown in FIG. 7 can be reduced to simply obtaining the digitized beat portion signal, matching the beat portion signal with a threshold value to determine presence or absence of the target substance, and then storing the presence or absence value with coordinates of the sensing volume. A more quantitative reading can be obtained by using a substance proportionality factor $SPF^o$ which is determined during a calibration step with the following relationship:

$$SPF^o = A^o / P_s^o \qquad (1)$$

where $A^o$ is the known amount of the target substance, and $P_s^o$ is the magnitude of the signal provided by the photodetector, for example voltage or current, which represents the optical effect on the beam pair within the sensing volume.

The parameters which affect the measured signal $P_s^o$ are represented by the relationship $$P_s^o = (P_{out}^o)(RCE_R^o)(T_o)^2(E_{opt}^o)(E_{det}^o)(E_s^o)(\Delta l^o)(A_o)(K) \qquad (2)$$

where $P_{out}^o$ is the output transmitter power, also referred to as laser power, $RCE_R^o$ is the receiver collection efficiency, $T^o$ is the transmission coefficient of the medium, $E_{opt}^o$ is the optical efficiency factor, $E_{det}^o$ is photodetector efficiency factor, $E_s^o$ is a physical proportionality factor such as flourescence efficiency for fluorescence or absorptivity for absorption, $\Delta l^o$ is a dimension of the sensing volume along the Z axis, and K is a constant determined during calibration. All of the above values are known during calibration. The value of $E_s^o$ for absorptivity, for example, is $1.1 \times 10^5$ Lmole$^{-1}$cm$^{-1}$ at wavelength $\lambda = 532$ nm for rhodamaine dye 6G (KODAK Laser Dyes, KODAK Publication JJ-169, 1987, Laboratory and Research Products Division, Eastman Kodak Company, Rochester, N.Y. 14650). The value of $E_s^o$ for fluorescence efficiency is the product of quantuum yield and absorptivity, for example, for rhodamine dye 6G in ethanol is $0.99 \times 10^5$ Lmole$^{-1}$CM$^{-1}$ at wavelength $\lambda = 532$ nm (same reference).

During sensing, the amount A determined by the relationship $$A = (P_s)(SPF^o)(F_{out})(F_{rec})(F\Delta l)F_{trans})(F_E) \qquad (3)$$

where A is the amount of the substance to be determined. $P_s$ is the received power, represented by the photodetector signal, which is affected by the amount of the substance, and factors $F_{out}$, $F_{rec}$, $F\Delta l$, $F_{trans}$, and $F_e$ are compensation factors to correct, that is, scale, the reading. These compensation factors are determined as follows: $F_{out}$ is determined by the relationship $$F_{out} = P^o{}_{out}/P_{out} \qquad (4)$$

where $P^o{}_{out}$ is the measured magnitude of the detector signal and $P_{out}$ is the present, that is, current, transmitter output power.

The receiver collection efficiency $RCE_R$ and sensing volume depth $\Delta l$ constant when the transmitter and detector optics have a constant F number. When it is not, a change in range is compensated for by the relationship $$F_{rec} = (R/R_o)^2 \qquad (5)$$

where R is the current range, as determined by the scanning unit, and $R_o$ is the initial range during calibration.

A change in sensitivity volume depth is compensated for by the relationship $$F\Delta l = \Delta l^o / \Delta l \qquad (6)$$

where $\Delta l$ is the current sensitivity volume depth, as determined by the current range, and $\Delta l^o$ is the initial sensitivity volume depth during calibration Transmission coefficient T compensates for the attenuation coefficient for the particular type of medium. Correction factor $F_{trans}$ is determined by $$F_{trans} = T^o/T \qquad (7)$$

Where
$$T^o = e^{-(AC_0)(R_O)} \qquad (8)$$

and
$$T = e^{-(AC)(R)} \qquad (9)$$

in which $AC_o$ is the calibration attenuation coefficient, AC is the attenuation coefficient for the present medium, $R_o$ is the calibration range and R is the present range. The attenuation coefficients are determined from lookup tables, such as Table I, below (made after Makoto Kikuchi and Yasuhisa Sakurai, in Laser Surgery, Part III, edited by I. Kaplan).

TABLE I

DEPTH OF LIGHT PENETRATION THROUGH VARIOUS TISSUES FOR VARIOUS WAVELENGTHS EXTINCTION LENGTH (mm)

| TISSUE | Laser/Wavelength | | | |
|---|---|---|---|---|
| | Argon/ 500 nm | He—Ne/ 630 nm | Ruby/ 690 nm | Nd—YAG/ 1060 nm |
| Liver | 0.41 | 0.76 | 1.03 | 1.76 |
| Stomach | 1.95 | 8.14 | 15.1 | 3.95 |
| Lung | 0.44 | 0.65 | 0.69 | 0.77 |
| Skin | 0.39 | 0.58 | 0.70 | 1.08 |

Factors $E_{opt}$ and $E_{det}$ are generally constant. Each may have a compensating factor for different spectra.

Physical proportionality factor $E_s$ is represented by the correction factor $F_E$ as follows:

$$F_E = E_s^o / E_s \tag{10}$$

where $E_s^o$ is the fluorescence efficiency for measuring fluorescence, of a known type and quantity of fluorescent material such as a photodynamic sensitizer, and $E_s$ is the fluorescence efficiency of that substance during the measuring condition. The fluorescence efficiencies for different compounds can be stored in the computer for access as needed.

Physical proportionality factor E can be dependent on the depth and type of tissue. These can be corrected by additional compensation factors determined empirically or calculated beforehand. Further, as is true of most of the above compensation factors, the actual values are typically wavelength dependent and therefore should be recalculated for analysis of different spectral lines.

The above procedure is greatly simplified for a differential system in which two or more channels are examined for each sensing volume. For calibration, the substance proportionality factor $SPF^o$ is defined as $$SPF^o = A^o / [P_r^o - P_s^o] \tag{11}$$

where $A^o$ is a known amount of the target substance, $P_R^o$ is the magnitude of the signal from the photodetector from a reference sensing volume and $P_s^o$ is the magnitude of the signal from the detector for the sensing volume in which the target substance is present. In other words, the first value is for the reference channel and the second value is for the substance channel. These values are simply measured, rather than being calculated as described above.

During sensing, the actual amount A to be determined is calculated from the expression $$A = [F_R P_R - F_s P_s](SPF^o)(F_E) \tag{12}$$

where $F_R$ is a scaling factor for the reference channel, determined by $$F_R = P_R^o / P_R \tag{13}$$

and $F_s$ is a scaling factor for the substance channel, expressed as:

$$F_s = P_s^o / P_R \tag{14}$$

Compensation factor $F_E$ is defined above in Equation 10. This value can be omitted if the conditions during sensing are the same as the conditions during calibration.

While the heterodyne system and method according to this invention have been described in terms of sensing fluorescence of a photodynamic sensitizer and differential absorption, these are not limitations of the invention. Any other optical effect can be utilized which can serve to distinguish a target substance from the surrounding medium.

In general, the term scattering refers to scattering or reflection based on absorption, or scattering based on different optical characteristics, such as density or reflection of the target substance. Further, some tissues naturally have fluorescence characteristics which can be utilized to distinguish them from surrounding tissue. For example, plaque on arterial walls has a different autofluorescence spectra from the spectra of normal wall tissue. In addition to reflection, a transmission system can be used, particularly in which the transmitter and/or receiver are configured as a fiber optic endoscope which can be inserted within a patient.

In addition to utilizing a heterodyne system according to this invention for detection and imaging, categorized as diagnostics, this system and method may also be used for therapy such as by controlling drug dosage before, during or after surgery and/or treatment using photodynamic sensitizers or other compounds which can be optically imaged. A heterodyne system and method according to this invention can also be used for light dosimetry to control the amount of light delivered during therapy, such as during photoactivation of chemical compounds. The system and method may also be used as a position sensor to determine the direction of treatment light to accurately impinge the light on the tumor during therapeutical treatment. Further, in addition to a target substance such as a bone or organ, presence of different substances in other environments can be sensed, such as the presence of water in a gasoline tank.

Although specific features of the invention are shown in some drawings and not others, this is for convenience only as each feature may be combined with any or all of the other features in accordance with the invention.

Other embodiments will occur to those skilled in the art and are with the following claims:

What is claimed is:

1. A system for sensing a target substance in a medium, comprising:

transmitter means for directing first and second beams of radiation to intersect within the medium and establish a sensing volume, the beams having different frequencies to generate a beat frequency at the sensing volume;

means for detecting a selected optical effect, based on an optical property of the target substance within the sensing volume, on the first and second beams at at least one selected spectral line and for generating a signal representative of the selected optical effect;

signal filter means for passing only the portion of the signal which is substantially at the beat frequency to produce a beat portion signal; and means for combining the beat portion signal with a selected value to determine the amount of the target substance.

2. The system of claim 1 in which said means for combining includes means for matching the beat portion signal with a threshold value as the selected value and for indicating when the threshold value is exceeded.

3. The system of claim 1 in which said means for combining combines the beat frequency portion signal with at least one substance proportionality factor as the selected value.

4. The system of claim 3 in which said means for combining includes means for multiplying each of a plurality of substance proportionality factors with corresponding portions of the beat portion signal representing the selected optical effect at successive selected spectral lines.

5. The system of claim 3 in which said means for combining includes means for multiplying a single said substance proportionality factor with a portion of the beat portion signal representing the selected optical effect at a plurality of selected spectral lines.

6. The system of claim 3 in which the substance proportionality factor represents a predetermined relationship between the amount of the target substance and the magnitude of the beat portion signal.

7. The system of claim 6 in which said means for combining includes means for storing the substance proportionality factor.

8. The system of claim 6 in which said means for combining includes means for calculating the substance proportionality factor according to the recited relationship.

9. The system of claim 1 in which said means for detecting includes means for measuring absorbance as the selected optical effect at the selected spectral line.

10. The system of claim 1 in which said means for detecting includes means for measuring fluorescence as the selected optical effect at the selected spectral line.

11. The system of claim 1 in which said means for detecting includes means for measuring scattering as the selected optical effect at the selected spectral line.

12. The system of claim 1 in which said transmitter means includes means for producing said first and second beams of radiation.

13. The system of claim 12 in which said means for producing includes first laser means for producing an initial beam, and beam splitter means for separating said initial beam into said first and second beams.

14. The system of claim 13 in which said transmitter means further includes means for shifting the frequencies of said first and second beams relative to each other.

15. The system of claim 13 in which said transmitter means further includes means for modulating said initial beam or said first and second beams at a predetermined frequency, and means for synchronizing the detection of the optical effect with said frequency.

16. The system of claim 1 in which said transmitter means includes scanning means for altering the directing of said first and second beams to relocate the sensing volume within the medium.

17. The system of claim 16 in which said scanning means produces a depth signal indicative of the depth of the sensing volume within the medium, and said means for combining includes means, responsive to said depth signal, for supplying a different selected value as the depth changes.

18. A system for sensing a target substance in a medium, comprising:
first transmitter means for directing first and second beams of radiation to intersect within the medium and establish a first sensing volume, the beams having different frequencies to generate a first beat frequency at said first sensing volume;
second transmitter means for directing third and fourth beams of radiation to intersect within the medium and establish a second sensing volume, the third beam having a different frequency from the fourth beam to generate a second beat frequency at said second sensing volume;
detector means for detecting a first selected optical effect, based on a first optical property of the target substance within said first sensing volume, on the first and second beams at at least one selected spectral line, for detecting a second selected optical effect, based on a second optical property of the target substance within said second sensing volume, on the third and fourth beams at at least one selected spectral line, and for generating a signal representative of said first and second selected optical effects;
signal filter means for passing only the portions of said signal which are substantially at said first and second beat frequencies to produce a beat portion signal; and
means for combining said beat portion signal with at least one selected value to determine the amount of the target substance.

19. The system of claim 18 in which said first and second transmitter means establish said first and second sensing volumes proximate each other.

20. The system of claim 19 in which said first and second transmitter means each include scanning means for altering the directing of said first and second beams and said and third and fourth beams, respectively, to relocate said first and second sensing volumes within the medium.

21. The system of claim 18 in which said first and second transmitter means generate said first and second beat frequencies at different frequencies.

22. The system of claim 18 in which said first transmitter means includes means for producing said first and second beams of radiation, and said second transmitter means includes means for producing said third and fourth beams of radiation.

23. A system for sensing a target substance in a medium, comprising:
transmitter means for directing first and second beams of radiation to intersect within the medium and establish a sensing volume, the beams having different frequencies to generate a beat frequency at the sensing volume;
means for detecting absorbance, based on the absorptivity of the target substance within the sensing volume, of the first and second beams at at least one selected spectral line and for generating a signal representative of the absorbance;
signal filter means for passing only the portion of the signal which is at the beat frequency to produce a beat portion signal; and
means for combining at least one substance proportionality factor with said beat portion signal, representing the absorbance at the selected spectral line, to determine the amount of the target substance.

24. A system for sensing a target substance in a medium, the target substance including a material which fluoresces when illuminated by radiation at a first wavelength, comprising:
transmitter means for directing first and second beams of radiation to intersect within the medium and establish a sensing volume, the beams having different frequencies to generate a beat frequency at the sensing volume, at least one of the first and second beams being substantially at the first wavelength;

means for detecting the fluorescence of the fluorescent material at at least one selected spectral line and for generating a signal representative of the fluorescence;

signal filter means for passing only the portion of the signal which is at the beat frequency; and means for combining at least one substance proportionality factor with the beat frequency portion of the signal to determine the amount of the target substance.

25. A method of sensing a stationary target substance in a medium, comprising:

directing first and second beams of radiation to intersect within the medium and establish a sensing volume, the beams having different frequencies to generate a beat frequency at the sensing volume;

detecting a selected optical effect, based on an optical property of the target substance within the sensing volume, on the first and second beams at at least one selected spectral line and for generating a signal representative of the selected optical effect; and combining the portion of the signal which is substantially at the beat frequency with at least one selected value to determine the amount of the target substance.

26. A method of sensing a target substance in a patient, comprising:

generating first and second beams of radiation at different frequencies to generate a first beat frequency at their intersection;

directing the first and second beams of radiation to intersect within the medium and establish a first sensing volume;

generating third and fourth beams of radiation at different frequencies to generate a second beam frequency at their intersection;

directing the third and fourth beams of radiation to intersect within the medium and establish a second sensing volume;

detecting a first selected optical effect, based on an optical property of the target substance within the first sensing volume, on the first and second beams at at least one selected spectral line and for generating a first signal representative of the first selected optical effect;

detecting a second selected optical effect, based on an optical property of the target substance within the second sensing volume, on the third and fourth beams at at least one selected spectral line and for generating a second signal representative of the second selected optical effect;

combining at least a first substance proportionality factor with the portion of the first signal which is substantially at the first beat frequency;

combining at least a second substance proportionality factor with the portion of the second signal which is substantially at the second beat frequency; and determining the amount of the target substance based on the combinations.

27. The method of claim 26 further including successively shifting the sensing volumes through the medium to successive positions and producing an image of the target substance based on successive determinations of the amount of the target substance at the successive positions.

* * * * *